(12) United States Patent
Francischelli et al.

(10) Patent No.: US 6,807,968 B2
(45) Date of Patent: Oct. 26, 2004

(54) METHOD AND SYSTEM FOR TREATMENT OF ATRIAL TACHYARRHYTHMIAS

(75) Inventors: David E. Francischelli, Anoka, MN (US); Rahul Mehra, Stillwater, MN (US)

(73) Assignee: Medtronic, Inc., Minneapolis, MN (US)

(*) Notice: Subject to any disclaimer, the term of this patent is extended or adjusted under 35 U.S.C. 154(b) by 525 days.

(21) Appl. No.: 10/015,690

(22) Filed: Dec. 12, 2001

(65) Prior Publication Data

US 2004/0059324 A1 Mar. 25, 2004

Related U.S. Application Data

(60) Provisional application No. 60/286,953, filed on Apr. 26, 2001.

(51) Int. Cl.[7] ............................................. A61B 18/18
(52) U.S. Cl. ......................... 128/898; 606/41; 606/51
(58) Field of Search ................... 128/898; 606/27–52, 606/101–102

(56) References Cited

U.S. PATENT DOCUMENTS

| | | | |
|---|---|---|---|
| 5,357,956 A | 10/1994 | Nardella | 128/642 |
| 5,575,766 A | 11/1996 | Swartz et al. | 604/53 |
| 5,596,995 A | 1/1997 | Sherman et al. | 128/736 |
| 5,685,878 A | 11/1997 | Falwell et al. | 606/49 |
| 5,688,267 A | 11/1997 | Panescu et al. | 606/41 |
| 5,718,701 A | 2/1998 | Shai et al. | 606/41 |
| 5,733,280 A | 3/1998 | Avitall | 606/23 |
| 5,871,523 A | 2/1999 | Fleischman et al. | 607/99 |
| 5,895,417 A | 4/1999 | Pomeranz et al. | 607/101 |
| 6,032,077 A | 2/2000 | Pomeranz | 607/101 |
| 6,045,550 A | 4/2000 | Simpson et al. | 606/42 |
| 6,096,037 A | 8/2000 | Mulier et al. | 606/49 |
| 6,133,592 A | 10/2000 | Kishimoto et al. | 257/190 |
| 6,142,944 A | 11/2000 | Li et al. | 600/453 |
| 6,161,543 A | 12/2000 | Cox et al. | 128/898 |
| 6,187,003 B1 | 2/2001 | Buysse et al. | 606/49 |
| 6,237,605 B1 | 5/2001 | Vaska et al. | 128/898 |
| 6,517,536 B2 * | 2/2003 | Hooven et al. | 606/41 |
| 6,701,931 B2 * | 3/2004 | Sliwa et al. | 128/898 |

FOREIGN PATENT DOCUMENTS

| | | |
|---|---|---|
| WO | WO 99/12488 | 3/1999 |
| WO | WO 99/59486 | 11/1999 |
| WO | WO 01/72234 | 10/2001 |
| WO | WO 01/80724 | 11/2001 |

* cited by examiner

Primary Examiner—Roy D. Gibson
Assistant Examiner—Pete Vrettakos
(74) Attorney, Agent, or Firm—Thomas G. Berry; Jeffrey J. Hohenshell

(57) ABSTRACT

A method of and a system for treatment of atrial tachyarrhythmias. The system includes a set of hemostats having elongated opposing jaws carrying mechanisms for applying ablation energy along the jaws. The jaws having straight and curved configurations selected to allow arrangement of the jaws of along opposite sides of walls of a patient's atrium. Treatment is accomplished by applying of ablation energy to the walls of a patient's artria to create lines of lesion corresponding generally to incisions employed in a Maze type procedure.

11 Claims, 19 Drawing Sheets

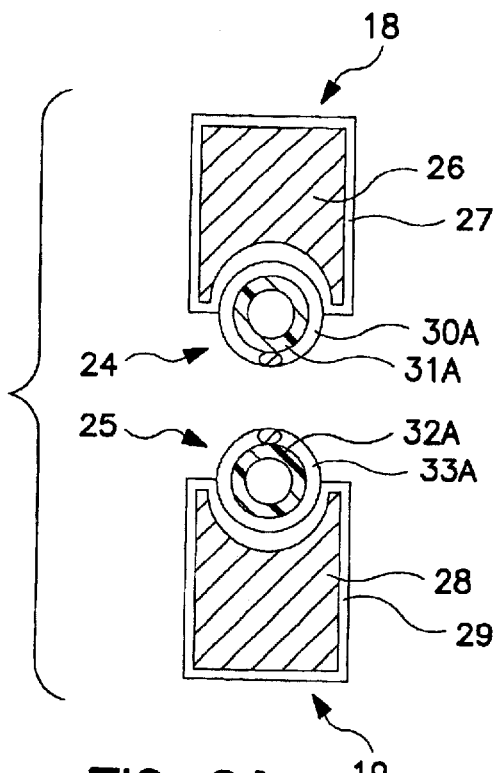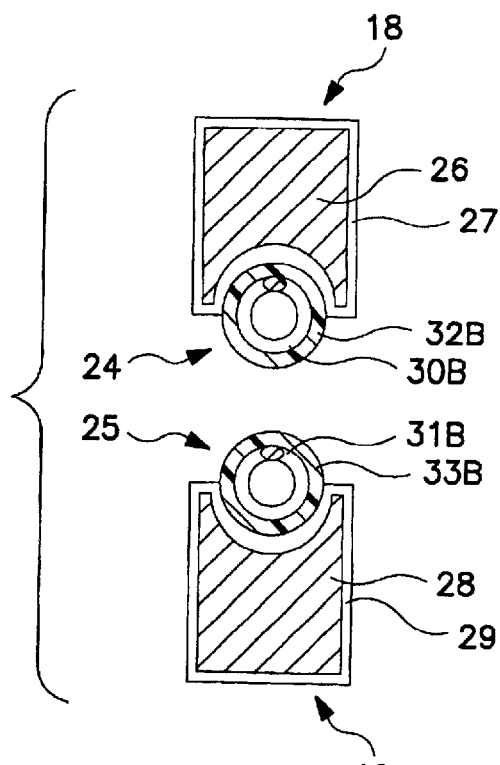
FIG. 2A  FIG. 2B
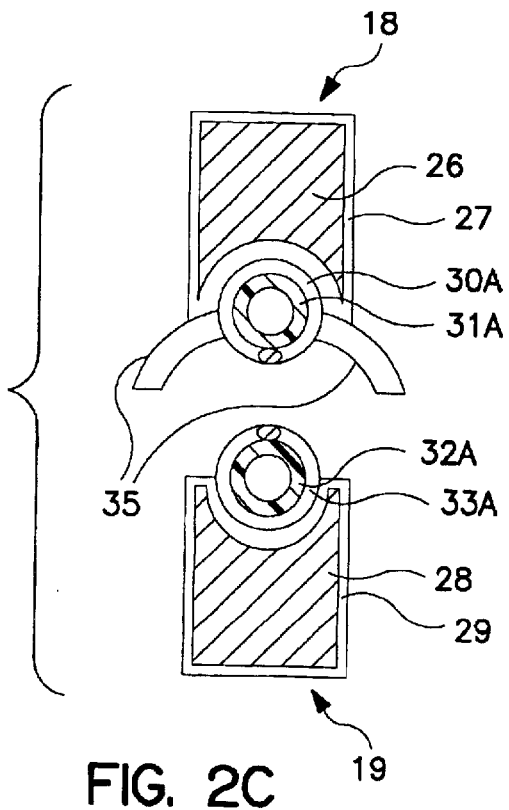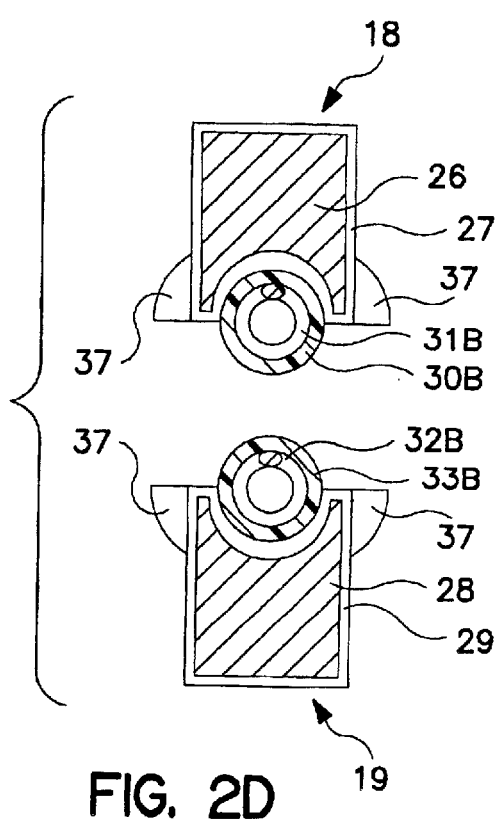
FIG. 2C  FIG. 2D

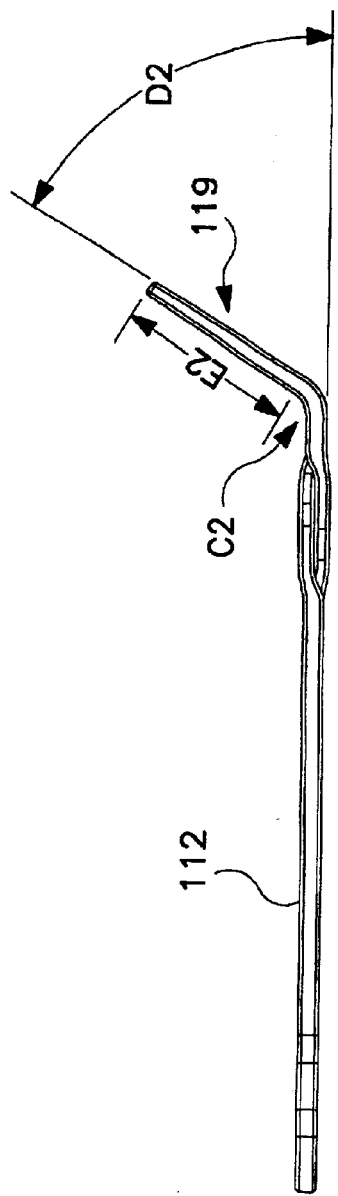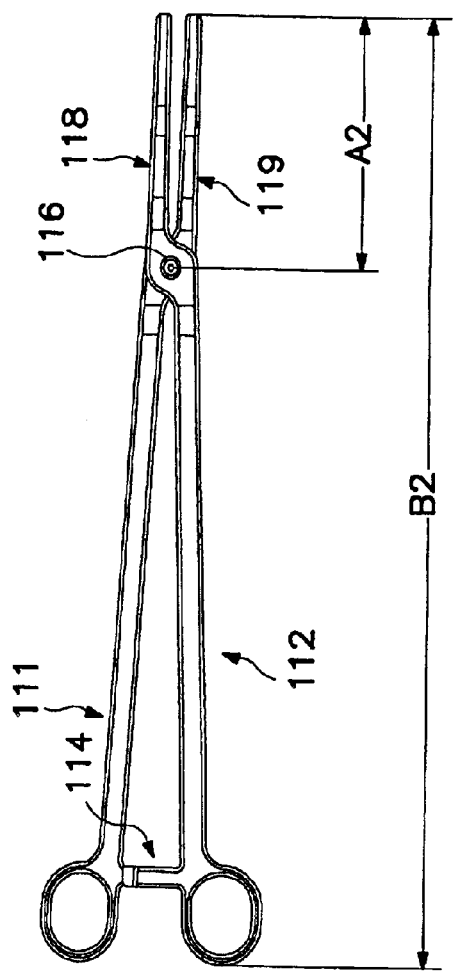
FIG. 3B
FIG. 3A

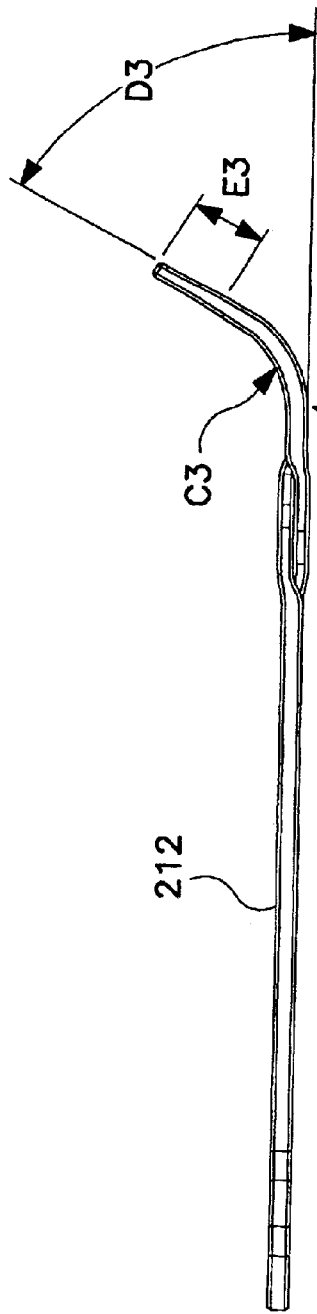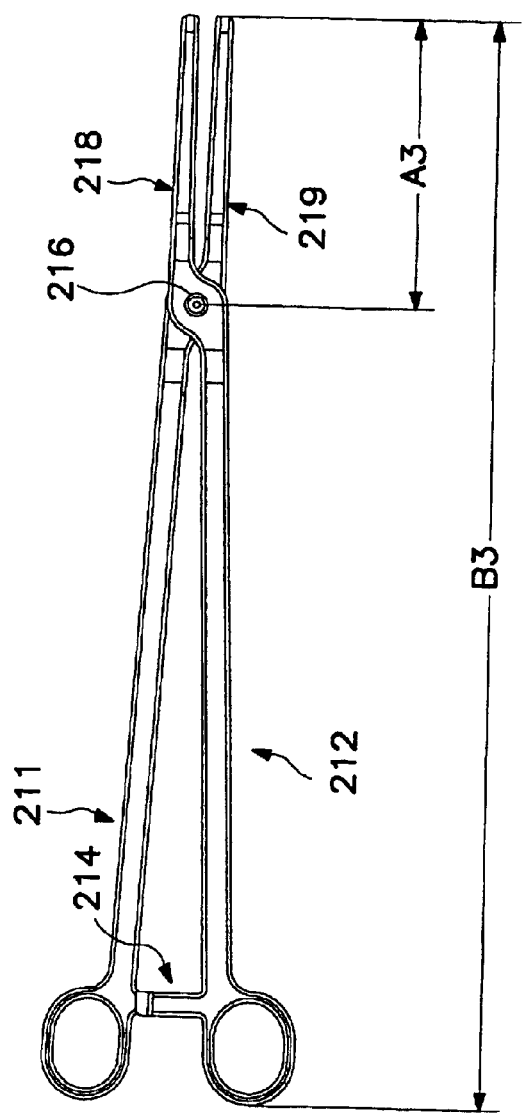

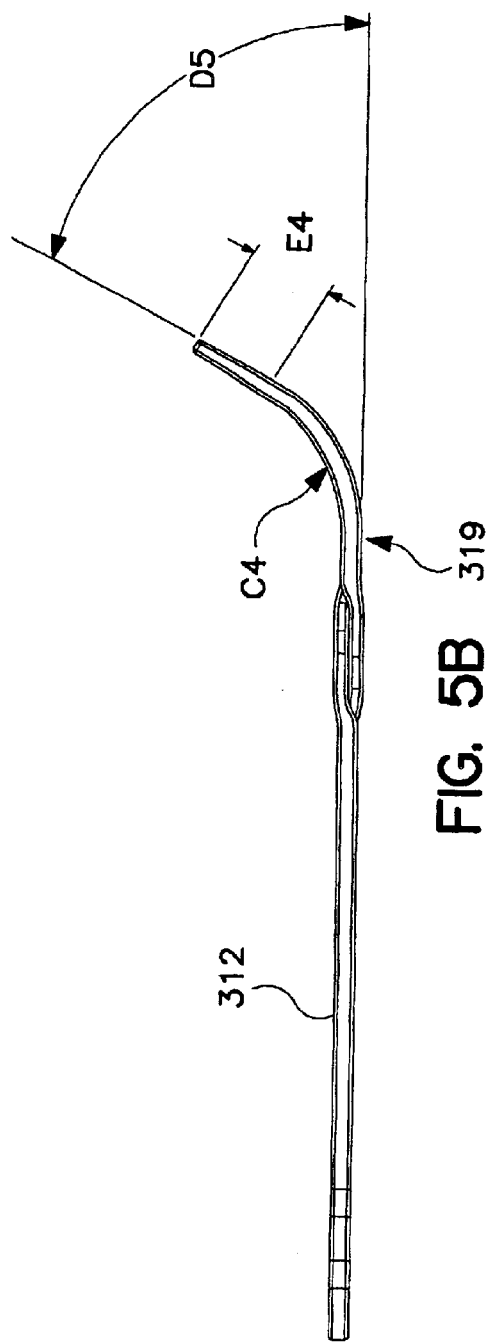
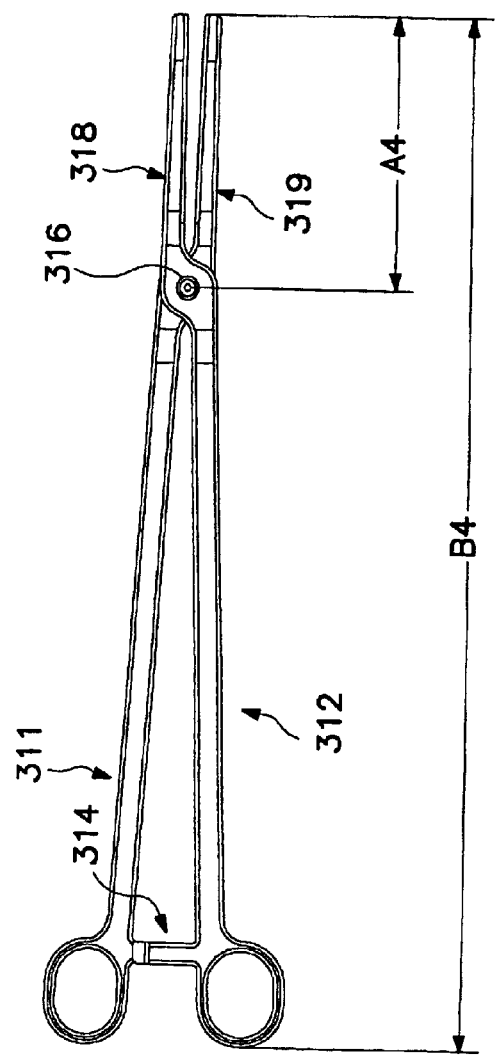

METHOD AND SYSTEM FOR TREATMENT OF ATRIAL TACHYARRHYTHMIAS

RELATED US APPLICATION DATA

This application claims priority from U.S. Provisional Patent Application No. 60/286,953, filed Apr. 26, 2001, incorporated herein by reference in its entirety.

BACKGROUND OF THE INVENTION

The present invention relates to surgical tools and procedures generally and relates more particularly to the use of electrosurgical ablation to treat atrial fibrillation.

In patients with chronic atrial fibrillation having tachycardia that resistant to medical treatment, the Maze III procedure has been employed. This procedure controls propagation of the depolarization wavefronts in the right and left atria by means of surgical incisions through the walls of the right and left atria. The incisions create blind or dead end conduction pathways, which prevent re-entrant atrial tachycardias from occurring. While the Maze procedure is successful in treating atrial fibrillation, the procedure is quite complex and is currently practiced by only a few very skilled cardiac surgeons in conjunction with other open-heart procedures. The procedure also is quite traumatic to the heart, as in essence the right and left atria are cut into pieces and sewed back together, to define lines of lesion across which the depolarization wavefronts will not propagate.

It has been suggested that procedures similar to the Maze procedure could be instead performed by means of electrosurgical ablation, for example, by applying RF energy to internal or external surfaces of the atria to create lesions across which the depolarization wavefronts will not propagate. Such procedures are disclosed in U.S. Pat. No. 5,895,417, issued to Pomeranz, et al., U.S. Pat. No. 5,575,766, issued to Swartz, et al., U.S. Pat. No. 6,032,077, issued to Pomeranz, U.S. Pat. No. 6,142,944, issued to Swanson, et al. and U.S. Pat. No. 5,871,523, issued to Fleischman, et al, all incorporated herein by reference in their entireties. Hemostat type electrosurgical or cryo-ablation devices for use in performing such procedures are described in U.S. Pat. No. 5,733,280 issued to Avitall, U.S. Pat. No. 6,237,605 issued to Vaska, et al, U.S. Pat. No. 6,161,543, issued to Cox, et al., PCT published Application No. WO99/59486, by Wang and in pending U.S. patent application Ser. No. 09/747,609 filed Dec. 22, 2000 by Hooven, et al., all incorporated herein by reference in their entireties. In order for such procedures to be effective it is desirable that the electrosurgically created lesions are continuous along their length and extend completely through the tissue of the heart. These goals may be difficult to accomplish employing dry ablation electrodes or electrodes applied only to the interior or exterior surfaces of the heart tissue.

SUMMARY OF THE INVENTION

According to the present invention, a maze type procedure may be performed using a set of bipolar electrosurgical hemostats, which apply ablation energy (e.g. RF energy) across the walls of the left and right atria by means of delivery means (e.g. electrodes) located on either side of the atrial walls. In a preferred embodiment of the invention, the hemostats are provided with elongated RF electrodes having various straight and curved configurations. In the particular embodiment of the invention described herein, a collection of straight and curved bipolar electrosurgical hemostats is provided in order to allow the physician to produce lines of lesion that approximate the incisions that would occur during the Maze III procedure as described in the book 'Cardiac Surgery Operative Technique' by Donald B. Doty, M.D. at pages 410–419, incorporated herein by reference in its entirety, and hereafter referred to as the "Doty reference". Other specific sets of hemostats may correspondingly be provided according to the invention to allow approximation of lines of lesion of the incisions that would be provided by other forms of the Maze procedure.

The invention as disclosed herein is describing the context of an open chest surgery, with patient undergoing cardiopulmonary bypass. As described, the procedure does include a limited number of surgical incisions, in conjunction with the creation of various straight and curved lesions using the bipolar electrosurgical hemostat set of the present invention. However, the present invention is also believed applicable to closed chest procedures, in which the heart is observed thoracoscopically and access is provided by means of thoracoscopic surgical ports. It is believed that ultimately, the invention may also applicable to closed chest, beating heart surgery, dispensing with the necessity of cardiac bypass.

A BRIEF DESCRIPTION OF THE DRAWINGS

Figure 1A:
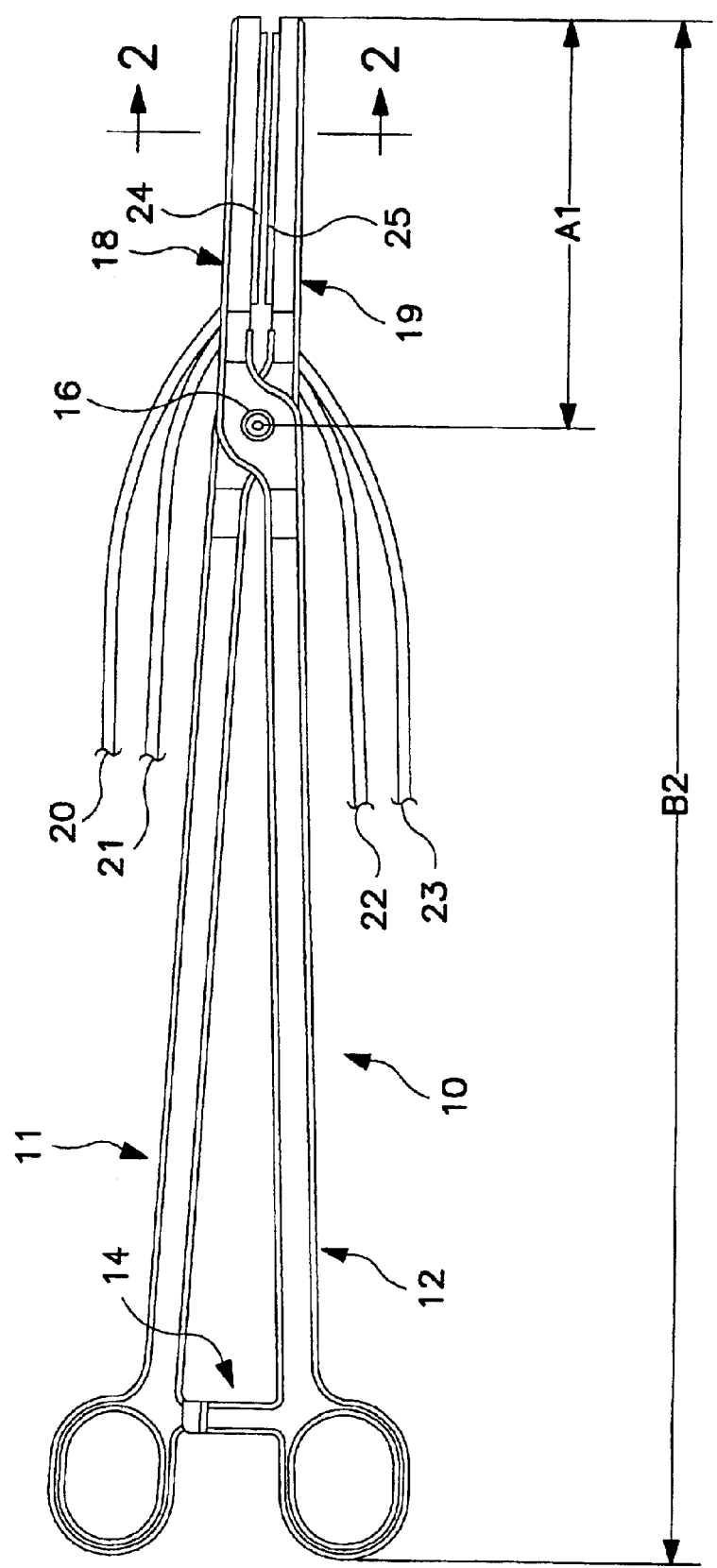
FIG. 1A illustrates a first embodiment of an electrosurgical hemostat according to the present invention having two elongated generally straight jaws.

FIGS. 2A, 2B, 2C and 2D all illustrate cross section through alternative configurations for electrodes carried by the jaws of the hemostat illustrated in FIG. 1A.

FIGS. 3A and 3B illustrate top and side views of a second electrosurgical hemostat according to the present invention.

FIGS. 4A and 4B illustrate top and side views of a third electrosurgical hemostat according to the present invention.

FIGS. 5A and 5B illustrate top and side views of a fourth electrosurgical hemostat according to the present invention.

FIGS. 6A through 6M are a series of drawings illustrating schematically the surgical procedure performed using the electrosurgical hemostats of the present invention and illustrating schematically the various incisions and lesions produced according to the present invention.

DETAILED DESCRIPTION OF THE PREFERRED EMBODIMENTS

The invention as disclosed in the present application includes a set of four pre-configured straight and curved hemostats, particularly optimized for performing an electrosurgical procedure mimicking the incisions provided according to Maze III surgical procedure. The set of hemostats is described in more detail below.

FIG. 1A illustrates a top plan view of the first of the four hemostats provided to the present invention. The hemostat may be approximately 31 centimeters in overall length as illustrated at B2, with draws of approximately 8 centimeters in length, as illustrated at A1.

The hemostat includes two elongated handle members 12 and 14, each provided with a finger loop at its proximal end. A conventional hemostat locking mechanism 14 is also provided. The handles of the hemostat may be fabricated of stainless steel or other readily resterilizable material. Alternatively, the handles 11 and 12 might be fabricated of a biocompatible plastic and/or the hemostat may be disposable.

To the jaws 18 and 19 of the hemostat extend distally from the pivot or hinge 16, and carry elongated electrosurgical electrodes 24 and 25. When the jaws are parallel to one another, electrodes 25 and 25 are preferably spaced approximately 0 to 7 mm from one another, more preferably 1 to 5 mm from one another, to facilitate uniform contact allng opposite sides of a patient's atrial wall. In use, the atrial wall is compressed between electrodes 24 and 25, and R-F energy is applied between the electrodes in order to create an elongated continuous lesion extending through the cardiac tissue. Using the hemostat of FIG. 1A, a linear lesion is produced.

The electrodes 24 and 25 are preferably configured to allow fluid—assisted tissue ablation, of the type generally described in U.S. Pat. No. 6,096,037, U.S. Pat. No. Mulier, incorporated herein by reference in its entirety. To this end, each of the electrodes is provided with an electrical conductor, 20, 23 allowing delivery of R-F electrical energy to the electrodes 24 and 25, respectively and with a fluid lumen 21, 22 allowing for delivery of saline solution or other conductive fluid to and along the length of electrodes 24 and 25. Various alternative embodiments of the electrodes and jaws of the hemostat of FIG. 1A are illustrated in FIGS. 2A through 2D, discussed below.

In use in a preferred embodiment of the invention, one jaw of the hemostat of FIG. 1A is inserted into the interior right or left atrium through an incision provided in the wall of the left or right atrium, while the other jaw remains outside of that chamber. The jaws are pressed together, somewhat compressing the atrial wall between the jaws, to provide for continuous contact along the length of the jaws on both sides of the atrial wall. RF energy is delivered between the electrodes. Control of delivery of energy or power to assure a complete lesion may be accomplished by measurement of impedance between the electrodes, as in U.S. Pat. No. 6,133,592, issued to Taylor, U.S. Pat. No. 5,718,701, issued to Shai, et al or U.S. Pat. No. 5,357,956, issued to Nardella, or allowed Pending U.S. application Ser. No. 09/347,635, filed Jul. 6, 1999 by Hoey et al, all incorporated herein by reference in their entireties. Alternatively, thermocouples or other temperature sensors may be added to the jaws of the hemostat and delivery of energy or power controlled as in U.S. Pat. No. 5, 685,878, issued to Falwell, et al., U.S. Pat. No. 6,045,550, issued to Simpson, et al., U.S. Pat. No. 5,688,267, issued to Panescu, et al or U.S. Pat. No. 5,596,995, issued to Sherman, et al., all also incorporated herein by reference in their entireties. As an additional alternative, delivery of energy or power may be time terminated, based upon empirically determined times found to lesions extending completely through the atrial walls at the power or energy levels chosen, or regulation of ablation energy by means of any of the references cited above may be employed if appropriate.

Figure 1B:
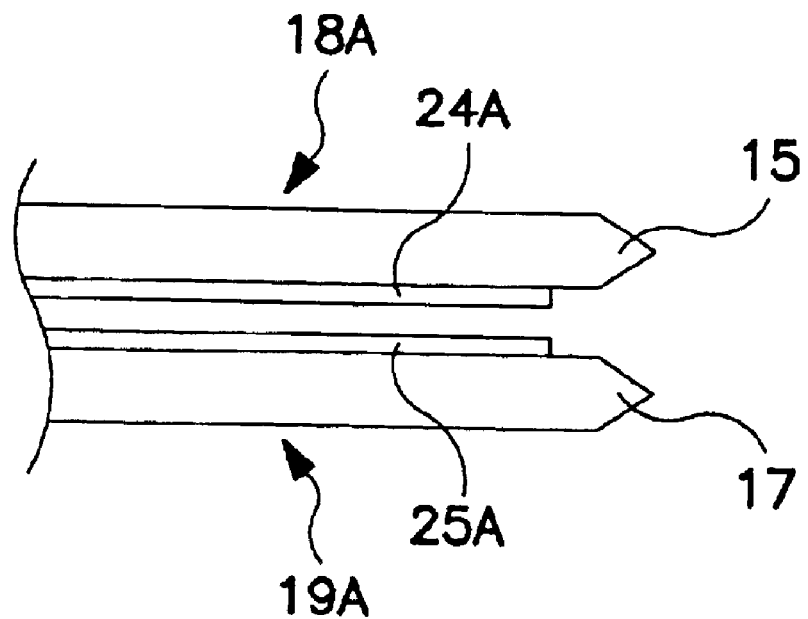
FIG. 1B illustrates an alternative configuration for the tips of the jaws of the hemostat illustrated in FIG. 1A.

It is anticipated that in some versions of the present invention which employ a more limited access approach to the heart, the distal tips of hemostat jaws themselves may be sharpened and used to pierce the atrial wall, eliminating the necessity of a separate incision. FIG. 1B illustrates such an alternative hemostat jaw construction, wherein hemostat jaws 18A and 19A correspond generally to jaws 18 and 19 in FIG. 1A, and carry electrodes 24A and 25A which also correspond to electrodes 24 and 25 in FIG. 1A. However, the distal tips 15 and 17 of the jaws are sharpened to a point or an edge so that either may be used to directly penetrate the atrial wall, eliminating the necessity of a separate incision.

FIGS. 2A through 2D are cross sectional views through the jaws of a hemostats as in FIG. 1A, illustrating possible alternative constructions. In FIG. 2A, the jaws 18 and 19 are made of a metallic core 26, 28, covered by an insulative coating or paint, 27, 29. Electrodes 24 and 25 take the form of elongated conductive coils, 30A, 33A, carrying tubes 31A, 32A, of expanded PTFE, through which a conducted fluid such as saline solution may be delivered along the length of the electrode coils 30A, 33A. The lumens of the EPTFE tubes 31A, 32A may be sealed at their distal extremities.

FIG. 2B illustrates a first alternative embodiment, corresponding generally to that illustrated in FIG. 2A, with elements corresponding to those identically numbered in in FIG. 2A. In this embodiment, the configuration of the conductive coil, 31B, 32B and the expanded PTFE tubes, 32B, 33B is reversed, so that the coils are located within the EPTFE tubes. As in the embodiment illustrated in Figure A, saline or other conductive fluid is delivered through the inner lumen of EPTFE tubes 32B, 33B.

FIG. 2C illustrates a third embodiment according to the present invention. In this case, elements also correspond to identically numbered elements in FIG. 2A. However, in the embodiment of FIG. 2C, elongated guides or flanges 35 are added in order to enhance longitudinal alignment of the jaws 18 and 19, along their length. When heart wall tissue is compressed between jaws 18 and 19, flanges 35 tend to retain jaws 18 and 19 and correspondingly electrode coils 30A and 33A in alignment with one another, through the intermediary of the atrial wall tissue.

FIG. 2D illustrates a fourth embodiment, corresponding generally to that illustrated in FIG. 2B, discussed above. Elements correspond to identically numbered elements in FIG. 2B. In addition, jaws 18 and 19 are each provided with elongated magnetic elements 37, arranged to assist in pulling jaws 18 and 19 toward one another when the jaws are closed around atrial wall tissue. Elements 37 may be formed of rare earth magnets, so that their mutual attraction provides additional compressive force along the length of jaws 18 and 19, enhancing contact with atrial wall tissue. In the case of embodiments in which the cross sectional size of jaws 18 and 19 is reduced in order to facilitate insertion into tight spaces, inclusion of magnets 37 is believed particularly valuable. The inclusion of magnets 37 is also believed particularly valuable in embodiments in which jaws 18 and 19 are fabricated of a less rigid material, for example a somewhat flexible plastic as opposed to a rigid metal such as stainless steel.

It should be understood that the above-described cross sectional illustrations of the configurations of the jaws of the hemostat of FIG. 1A also apply to the construction of the jaws of the other three hemostats discussed below in conjunction with the present invention. The spacing between the electrodes on the jaws of these hemostats should also be understood to correspond to that of the hemostat of FIG. 1A. As such, electrode configurations for the hemostats of FIGS. 3A–5B are not discussed separately herein. Similarly, while conductors and fluid lumens are not illustrated in FIGS. 3A–5B, they should be understood to be present and correspond to those as illustrated in FIG. 1A. In addition, sharpened jaw tips as illustrated in FIG. 1B may also be employed.

FIGS. 3A and 3B illustrate top and side views, respectively, of a second hemostat according to the present invention. In this case, the hemostat is provided with first and second handle portions 111 and 112, which correspond to handles 11 and 12 of the hemostat illustrated in FIG. 1A, and is also likewise provided with a locking mechanism 114. The jaws 118 and 119 correspond generally in structure to the jaws 18 and 19 of the hemostat of FIG.1, however, in this case, the jaws 118 and 119 are bent to describe a generally straight distal portion extending over a length E2, which may be, for example, 5½ centimeters. The jaws are bent at C2 around a radius of approximately 0.5 centimeters and describe an angle D2 of approximately 60 degrees, as illustrated. The overall length of the hemostat B2 may be, for example, 23 centimeters, with the overall length of the jaws as illustrated at A2 being, for example, about 6½ centimeters from pivot 116 to the distal ends of the hemostat jaws, as measured in the plane defined by the handle members 111 and 112.

FIGS. 4A and 4B similarly illustrate top and side views of a third hemostat according to the present invention. Like the previous hemostats, this hemostat is provided with handled portions 211 and 212 and a conventional locking mechanism 214. Like the hemostat illustrated in FIGS. 3A and 3B, jaws 219 and 219 of this hemostat are similarly bent out of the plane defined by the two handled portions 211 and 212. In this case, the jaws 218 and 219 are bent to define a distal, generally straight portion E3 extending for approximately 2 centimeters, and are bent around a radius C3 of approximately 3 centimeters, to define an angle D3 of approximately 65 degrees. The overall length of the hemostat as measured in the plane defined by the handles 211 and 212 is approximately 26 centimeters, and the length of A3 of the jaws, as measured along the plane defined by the handles 211 and 212 is approximately 6 centimeters.

FIGS. 5A and 5B illustrate a fourth hemostat according to the present invention. Like the other hemostats, it is provided with handled portions 311 and 312 and a locking mechanism 314. This hemostat also displays a curved configuration, with jaws 318 and 319 bent upward out of plane defined by the handled portions 311 and 312, to define a generally straight distal portion extending over a length E4 of approximately 3 centimeters, and around a radius C4 of approximately 5 centimeters to define an angle D5 of approximately 60 degrees. As measured along the plane defined by handle 311 and 312, the overall length B4 of the hemostat is approximately 29 centimeters and the length A4 of the jaws extending from hinge 316 to the distal tips of jaws is approximately 9 centimeters.

FIGS. 6A–6M are schematic drawings which illustrate a procedure performed using the bipolar electrosurgical hemostats described above to obtain a result analogous to the Maze III procedure as described in the Doty reference cited above. The lines of lesion produced using the hemostats correspond to incisions as described in this reference, and the correspondence of the lesions to the incisions is described below.

Figure 6A:
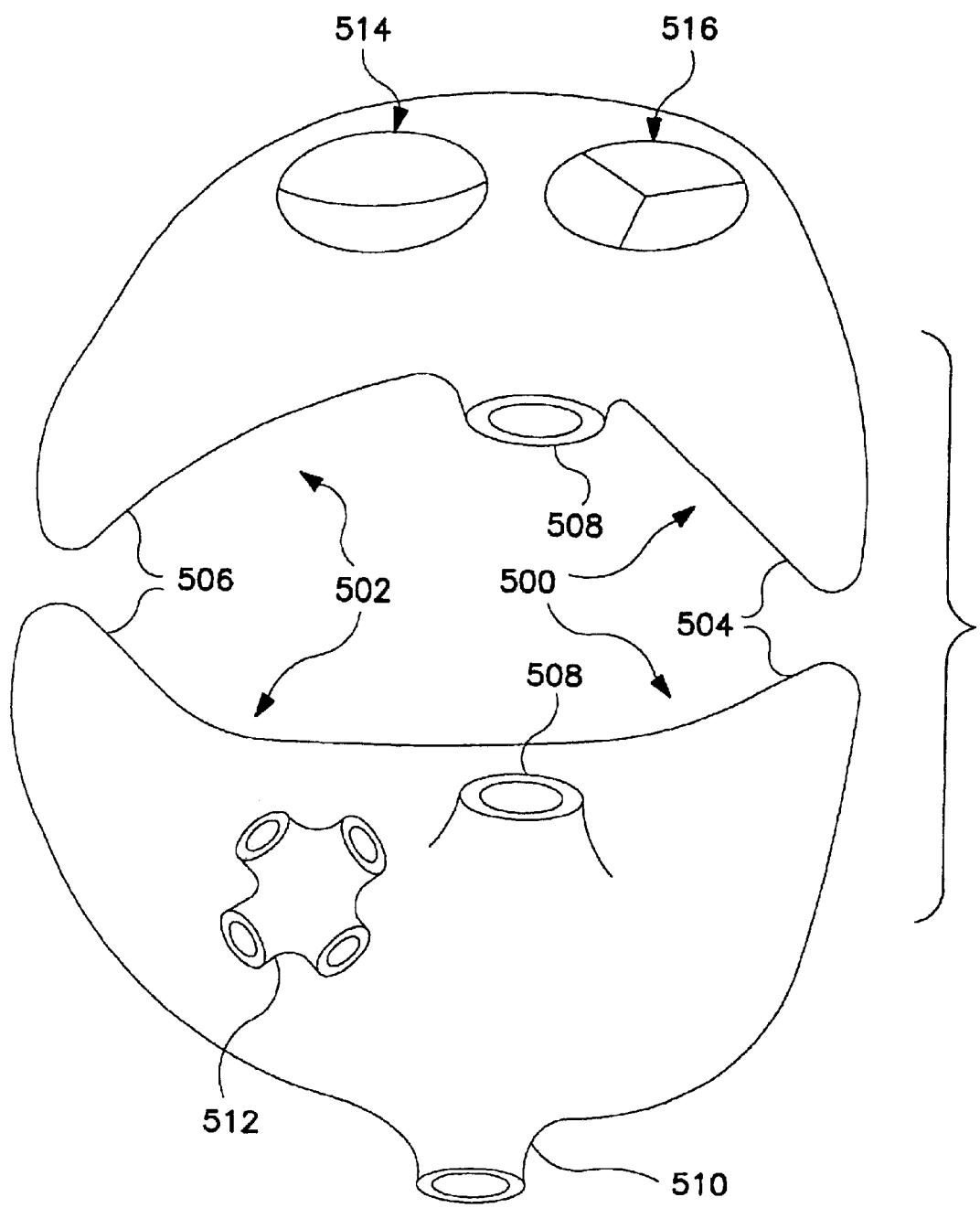

FIG. 6A is a schematic drawing illustrating the structure of the right and left atria, 500, 502, respectively, as viewed from a lower aspect, including tricuspid valve 16 and mitral valve 14 and as viewed from a more superior aspect, including the bases of the pulmonary veins 512 and the bases of the superior vena cava and inferior vena cava, 508 and 510 respectively, which enter the right atrium 500. The right and left atrial appendages are also illustrated schematically at 504 and 506, respectively. The structures as illustrated in FIG. 6A are correspondingly numbered in FIGS. 6B through 6M below.

Figure 6B:
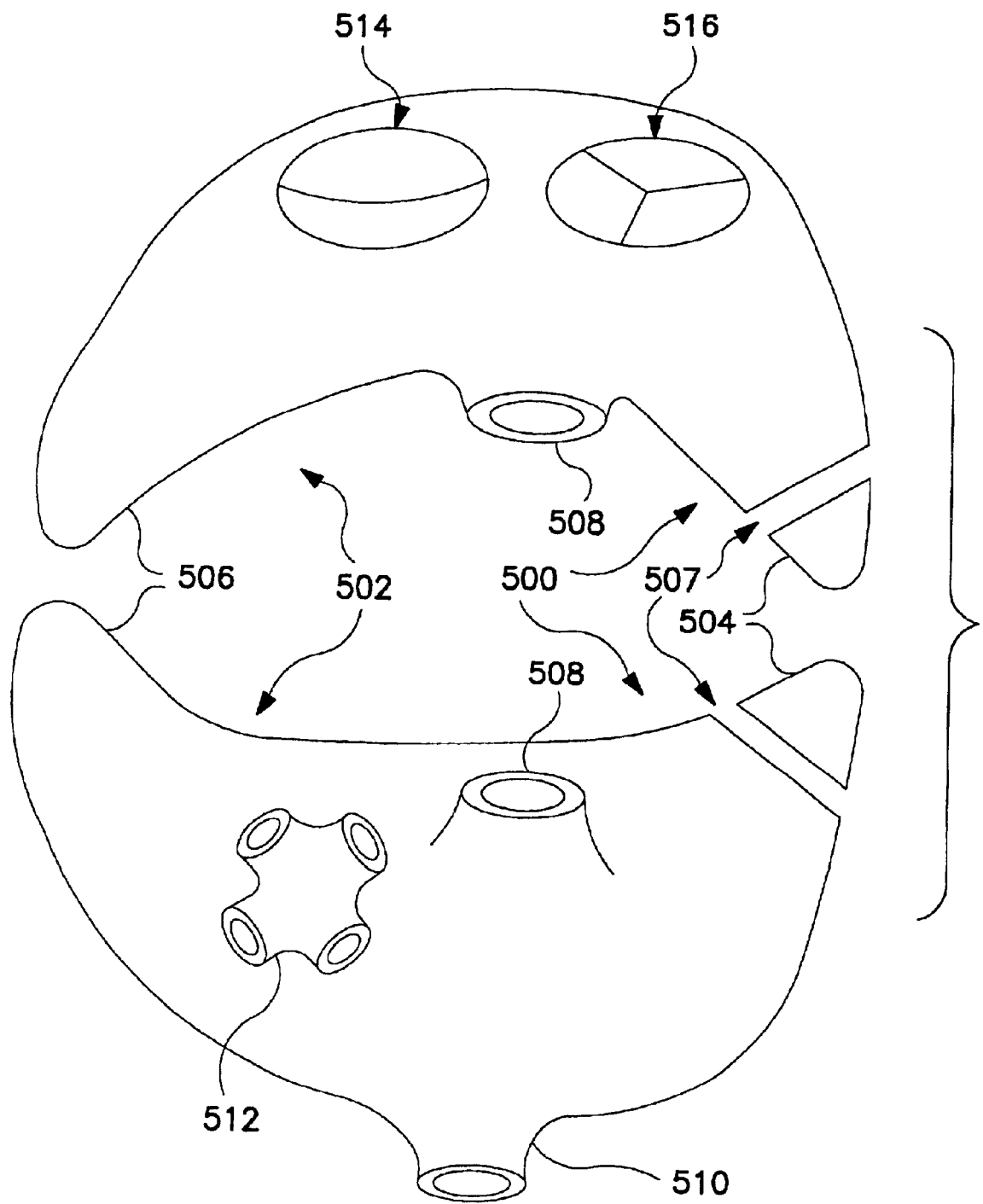

For purposes of understanding the basic method of the present invention as illustrated, it should be assumed that the operation is undertaken as an open chest operation, with the heart stopped and the patient on full bypass. Modifications to the procedure, in case of a limited access, stopped heart procedure and/or a limited access, beating heart procedure, are also generally described. FIG. 6B illustrates the first step of the procedure, comprising removal of the right atrial appendage 504. Right atrial appendage 504 is removed by means of an incision 507, which may be made by means of a scalpel or scissors. In a context of a closed chest procedure on either a beating or a stopped heart, a thoracoscopic tool may be substituted, preferably one capable of simultaneously cutting and stapling the remnant of the right atrial appendage.

Figure 6C:
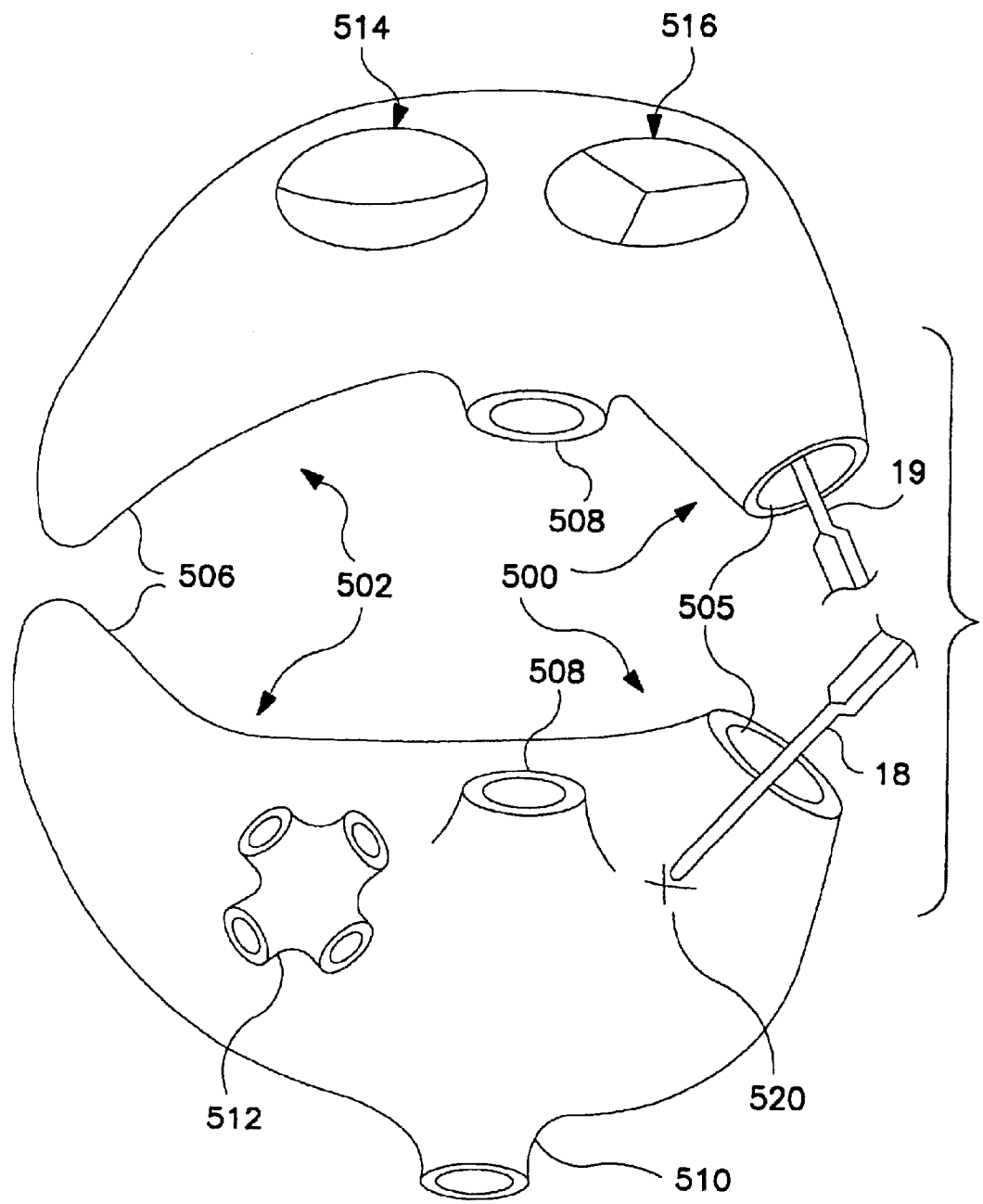

FIG. 6C illustrates the second step of the procedure, as performed using an open chest approach. During the second step, the electrosurgical hemostat of FIG. 1A is employed, with one jaw (19) of the hemostat inserted into the right atrium through the opening left by removal of the right atrial appendage and the other jaw arranged along the exterior surface of the heart. Jaws 18 and 19 are inserted until they extend to a point 520 located approximately at the mid point of the right atrium, approximately 5 centimeters from the opening 505 left by removal of the right atrial appendage. The jaws 18 and 19 are compressed and RF energy is applied between the electrodes located in jaws 18 and 19 to create an elongated lesion, extending through the tissue of the right atrial wall, to provide a block against passage of depolarization waves. For purposes of the following drawings, the placement of various hemostats will be described, but not specifically illustrated. Instead, the lesions to be produced by the hemostats will be illustrated by means of beaded lines, so that their interconnection and their relationship to the structures of the left and right atria 502, 500, may be understood. It should be understood that the hemostats are to be placed with their jaws extending along the lines of lesion as illustrated, unless otherwise specified.

In closed chest, limited access procedures, it is anticipated that the lesion produced may be made by inserting the jaw of an electrosurgical hemostat as illustrated in conjunction FIG. 1A, but having a sharpened tip as illustrated in FIG. 1B, directly through the heart wall at point 520, and the jaws advanced to the sealed remnant of the removal of the right atrial appendage to define a corresponding lesion.

Figure 6D:
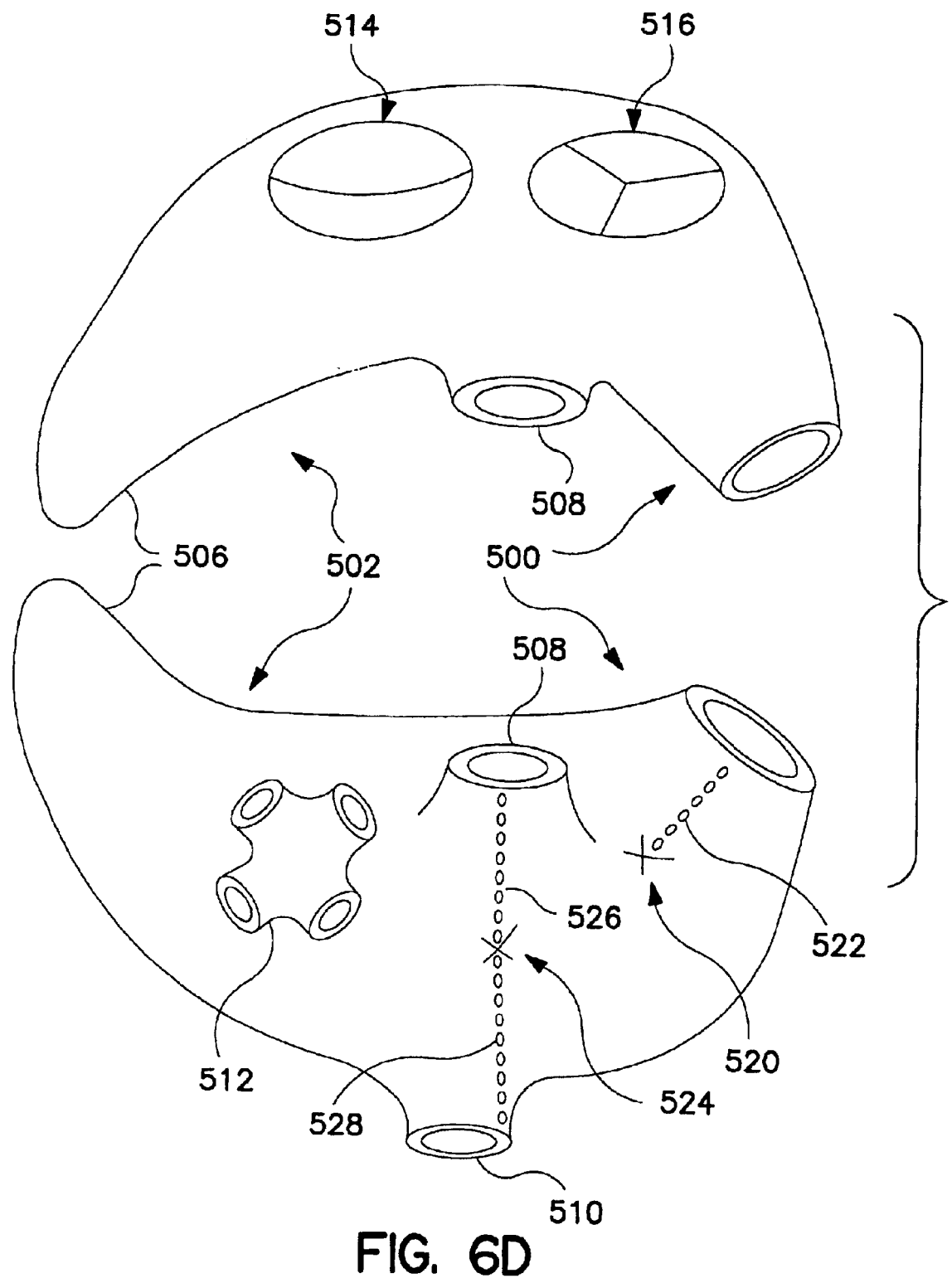

FIG. 6D illustrates the next step in the procedure and also illustrates lesion 522 produced by the application of the electrosurgical hemostat as illustrated in FIG. 6C. Lesion 522 corresponds generally to the incision illustrated at step A1 as described in the Doty reference. At 524, a local access incision is cut, at a point approximately midway between the inferior vena cava and superior vena cava (510, 508). Lesions 526 and 528, extending from access incision 524 to the superior and inferior vena cava, respectively, are produced by inserting one jaw of a hemostat as illustrated in FIG. 1A through the access incision 524 and arranging the jaws of the hemostat to extend on either side of atrial tissue from the incision 524 to the superior vena cava and inferior vena cava, respectively. Alternatively, a hemostat as illustrated in FIGS. 3A and 3B might be employed, with atrial tissue compressed between the straight, distal portions of the jaws. The lesions 528 and 526 so produced correspond to the incisions illustrated at step B as described in the Doty reference. In more limited access surgeries, hemostats having sharpened jaws as illustrated in FIG. 1B might be employed, with the sharpened tip of a jaw employed to create the access incision 524.

Figure 6E:
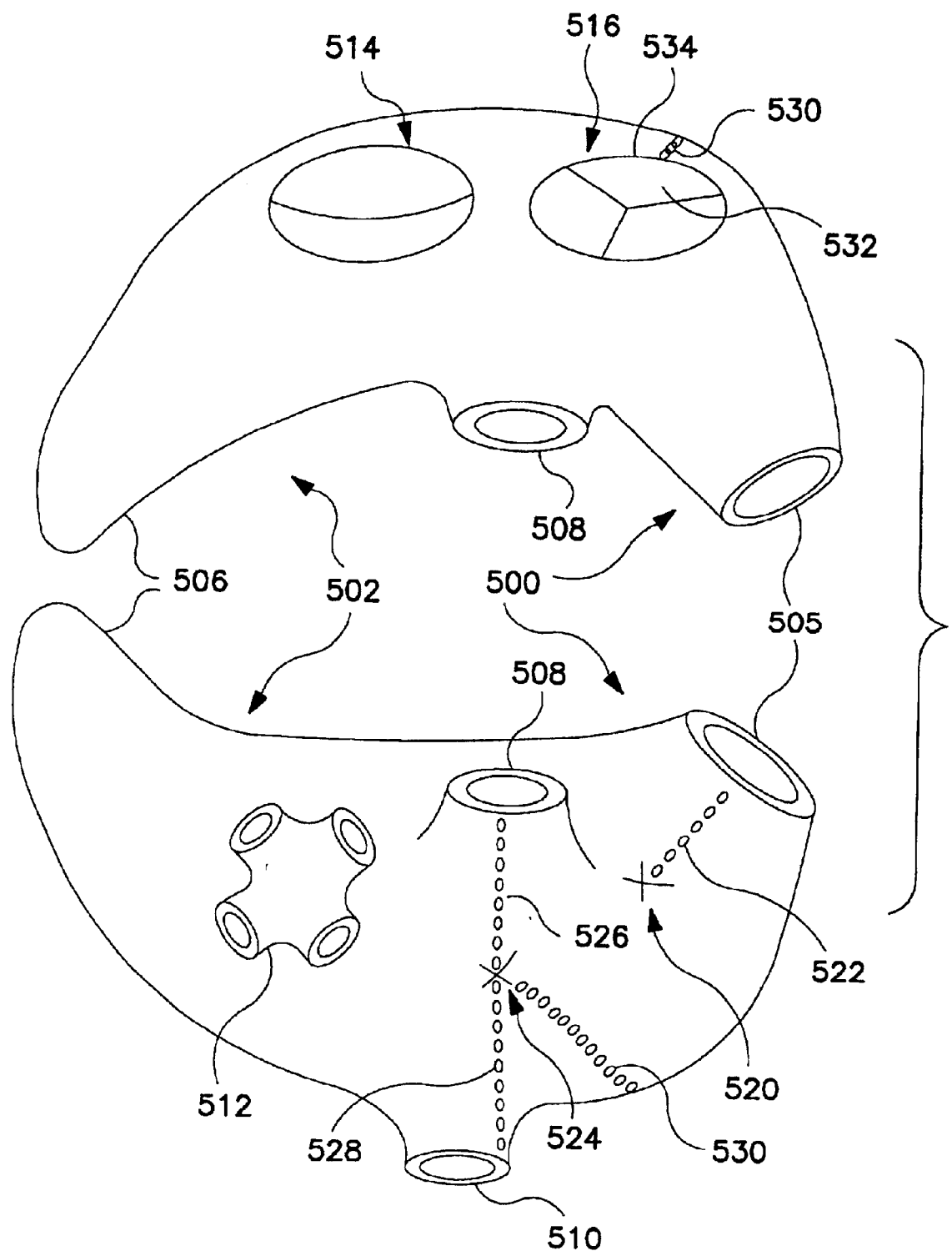

FIG. 6E illustrates the next step in the procedure. In this step, one jaw of a hemostat as illustrated in FIG. 1A or as illustrated in FIGS. 3A and 3B is inserted through access incision 524, and the jaws are arranged along either side of the atrial wall to create lesion 530, extending to the annulus of tricuspid valve 516, terminating at a point 534 approximately at the center of the posterior leaflet 532. This lesion should extend as close as possible to the tricuspid annulus. This lesion corresponds generally to the incision illustrated at steps D and E as described in the Doty reference. Optionally, cryo-ablation may be performed to complete the lesion at the tricuspid annulus at the terminus of lesion 530, by means of a cryo-probe inserted through the opening 505 in the remnant of the right atrial appendage. Cryo-ablation corresponds generally to that illustrated at step F as described in the Doty reference. In more limited access surgeries, the cryo-probe might be inserted through access lesion 524 or might be inserted transvenously.

Figure 6F:
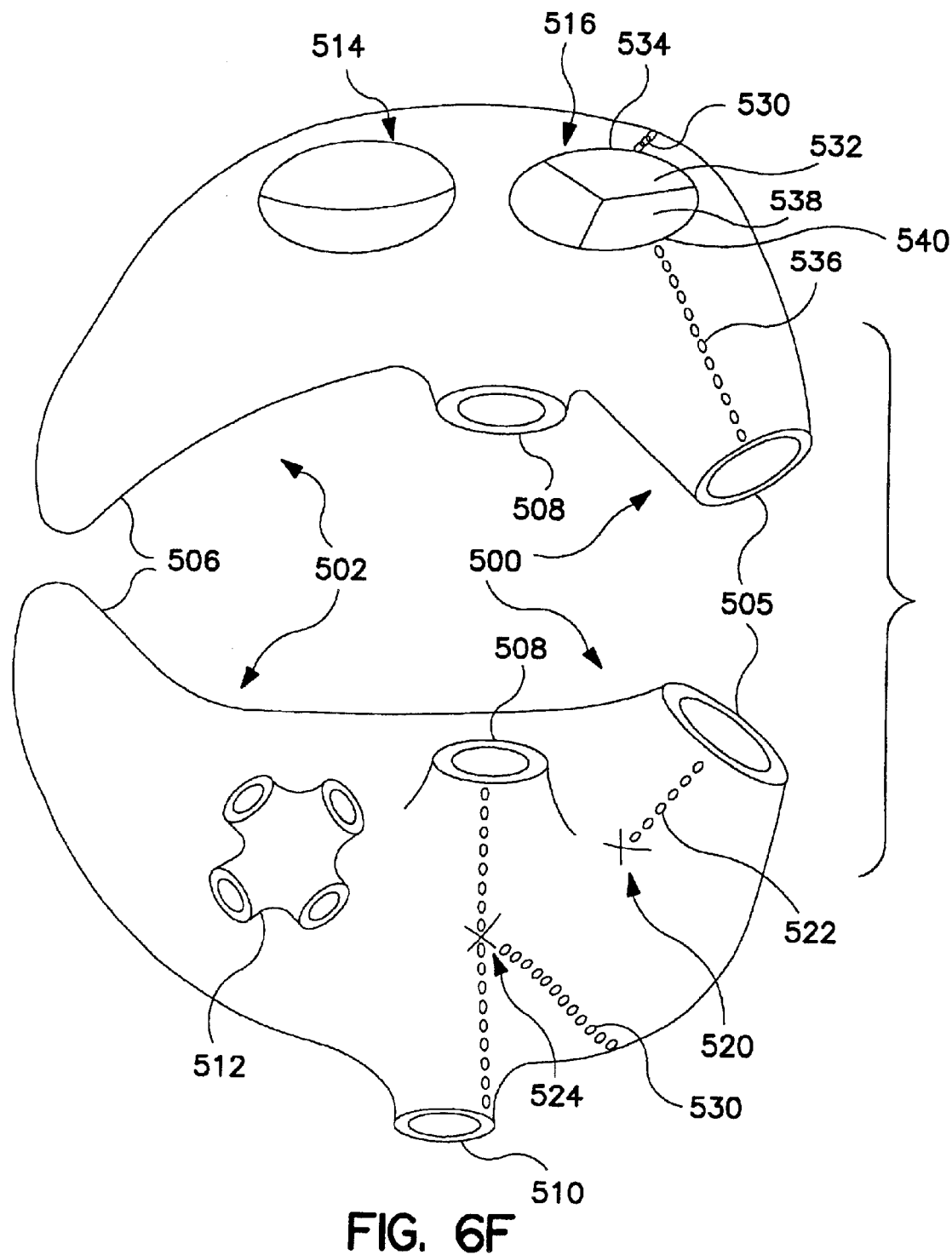

FIG. 6F illustrates the next step of the procedure. In FIG. 6F, lesion 536 is created using the distal portion of the jaws of a hemostat as in FIG. 1A. One jaw of the hemostat is inserted through the opening 505 in the remnant of the right atrial appendage, and the jaws are arranged to extend along either the right atrial wall to the annulus of the tricuspid valve 516 at the midpoint of the anterior leaflet 538. This lesion corresponds generally to the incision illustrated at steps H and I as described in the Doty reference. Care must be taken during this step to avoid the right coronary artery. Optionally, cryo-ablation may be applied at the tricuspid annulus at point 540, at the termination of lesion 536. Again, cryo-ablation may be provided by means of a cryo-probe inserted via the opening 505 in the remnant of the right atrial appendage, through access lesion 524, or, alternatively be means of a cryo-probe inserted transvenously. Cryo-ablation corresponds generally to that illustrated at step J as described in the Doty reference.

Figure 6G:
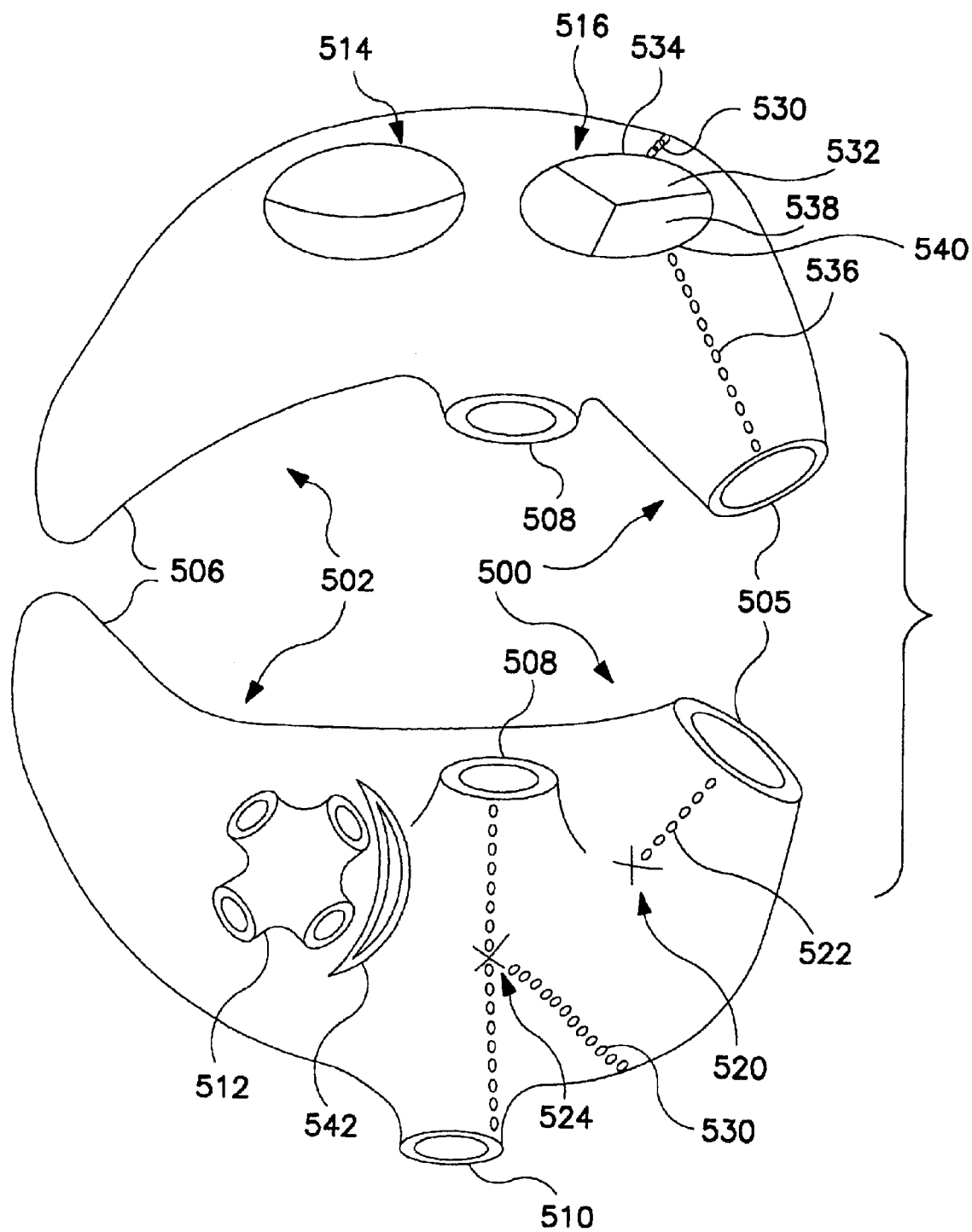

FIG. 6G illustrates the next step of the procedure which is the creation of an incision 542 extending through the left atrial wall, posterior to the inter atrial groove, near the orifices of the right pulmonary veins. In an open chest procedure, incision 542 may be made conventionally by means of scissors or a scalpel. Incision 542 corresponds to the incision illustrated at step K as described in the Doty reference. In more limited access surgeries, incision 542 might be replaced by a simple access incision made by means of the sharpened tip of one of the jaws of the hemostats used to create the lesions surrounding the orifices of the pulmonary veins, as discussed below.

Figure 6H:
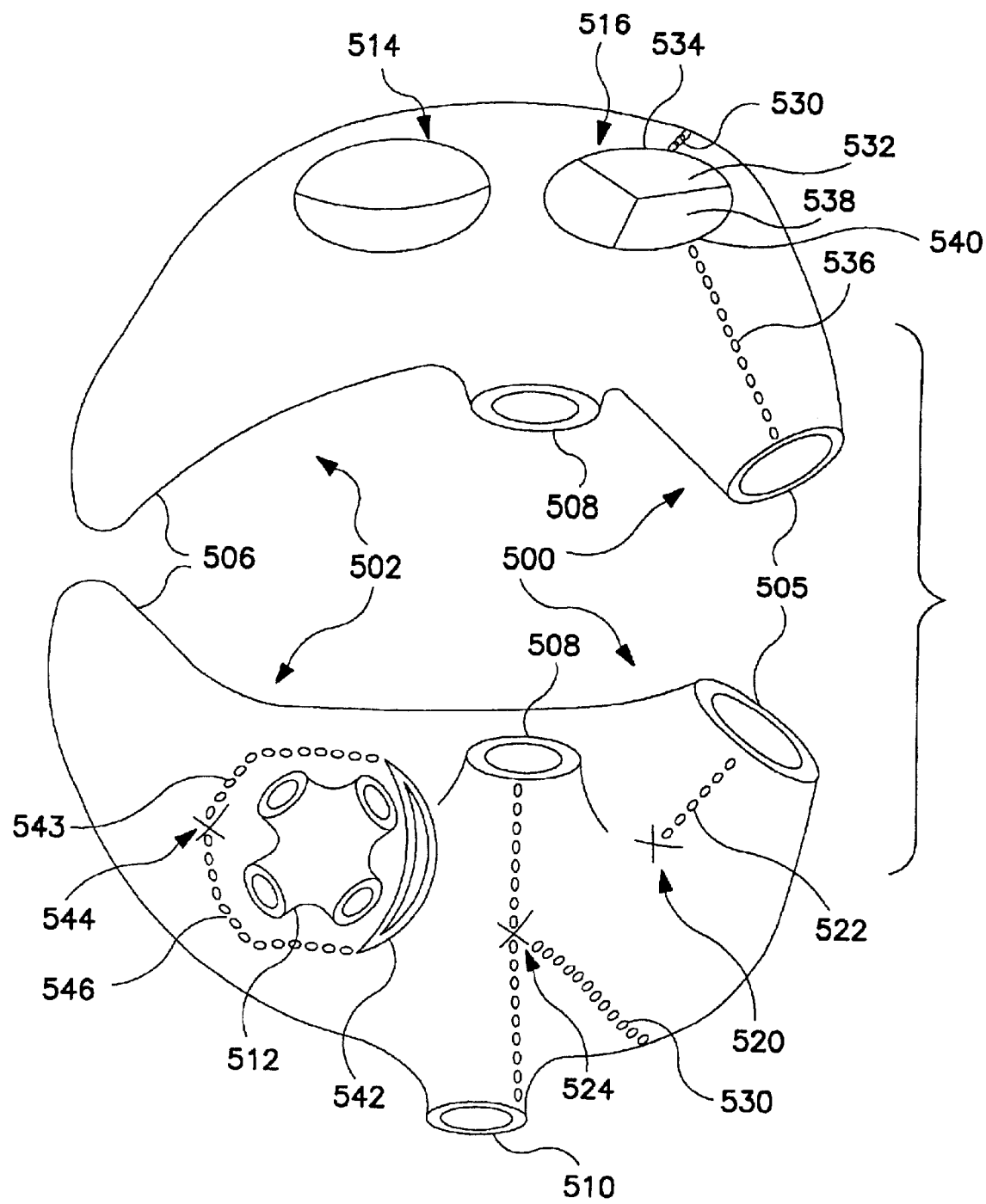

FIG. 6H illustrates the next step of the procedure, which is the creation of lesions 543 and 546. Lesions 543 and 546 may be accomplished by insertion of a hemostat having curved jaws as illustrated in FIGS. 5A and 5B, reversing the orientation of the hemostat between lesions, to create lesions extending around the base of the pulmonary veins 512 and meeting at a point 544, to complete the line of lesion. Incision 542 completes the line of lesion encircling the bases of the pulmonary veins. Lesions 543 and 546 correspond generally to the incisions illustrated at steps L and N as described in the Doty reference. In an alternative procedure, Lesions approximating the incisions illustrated at steps L and N may be produced by compressing the atrial wall tissue adjacent the bases of the left pulmonary veins between jaws of the hemostat illustrated in FIG. 4A or 5A applied epicardially to produce a lesion encircling the bases of the left pulmonary veins and repeating the procedure to correspondingly produce a lesion encircling the bases of the right pulmonary veins.

Figure 6I:
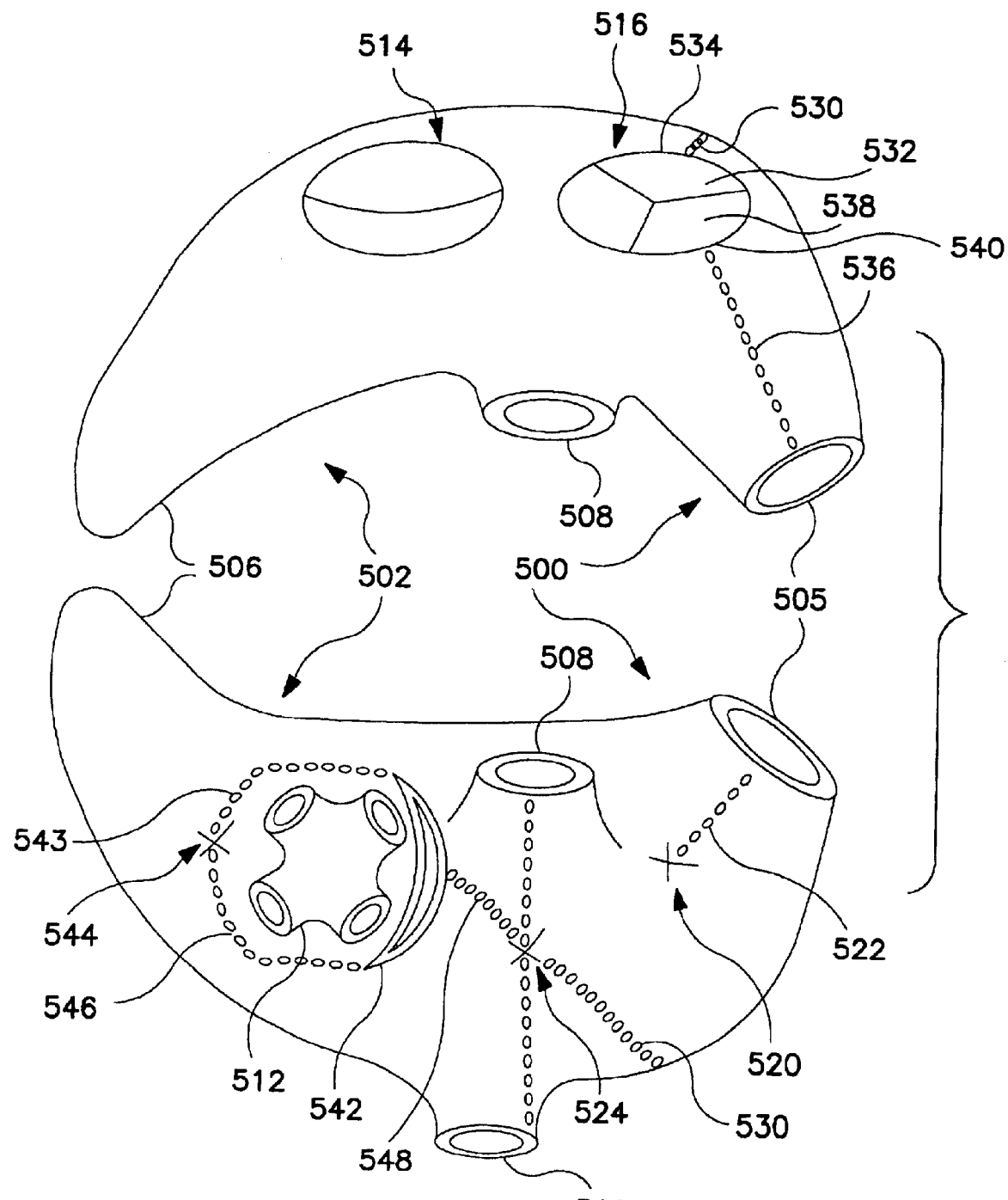

FIG. 6I illustrates the next step of the procedure, in which a hemostat having more sharply curved jaws, as illustrated in FIGS. 4A and 4B is employed to create lesion 548. Lesion 548 is created by inserting the jaws of the hemostat illustrated in FIGS. 4A and 4B, one into incision 542, the other into access incision 524, and compressing the atrial septum therebetween. The jaws are arranged so that they define a curved lesion extending along the atrial septum, extending to a point above the fossa ovalis, near but not into the tendon of Todaro. As the atrial septum is not visible in FIG. 6J, lesion 544 should be understood to correspond to the incision illustrated at step M as described in the Doty reference.

Figure 6J:
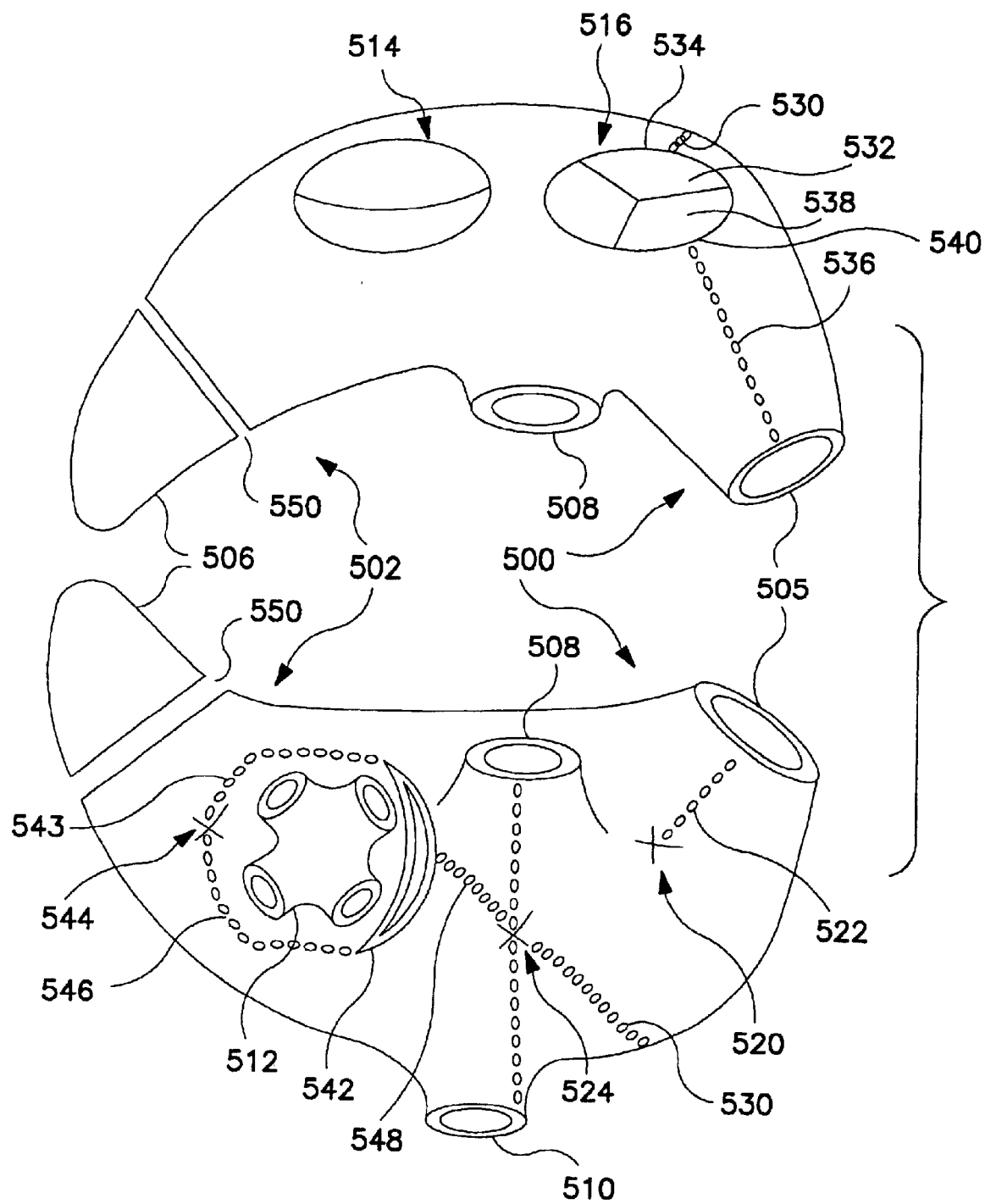

FIG. 6J illustrates the next step in the procedure, comprising the removal of left atrial appendage 506 by means of an incision 550. In open chest procedures, this incision might be made by means of a scissors or scalpel. In more limited access surgeries, this incision might be made by means of a thoracoscopically introduced, preferably one capable of simultaneously cutting and stapling the remnant of the right atrial appendage.

Figure 6K:
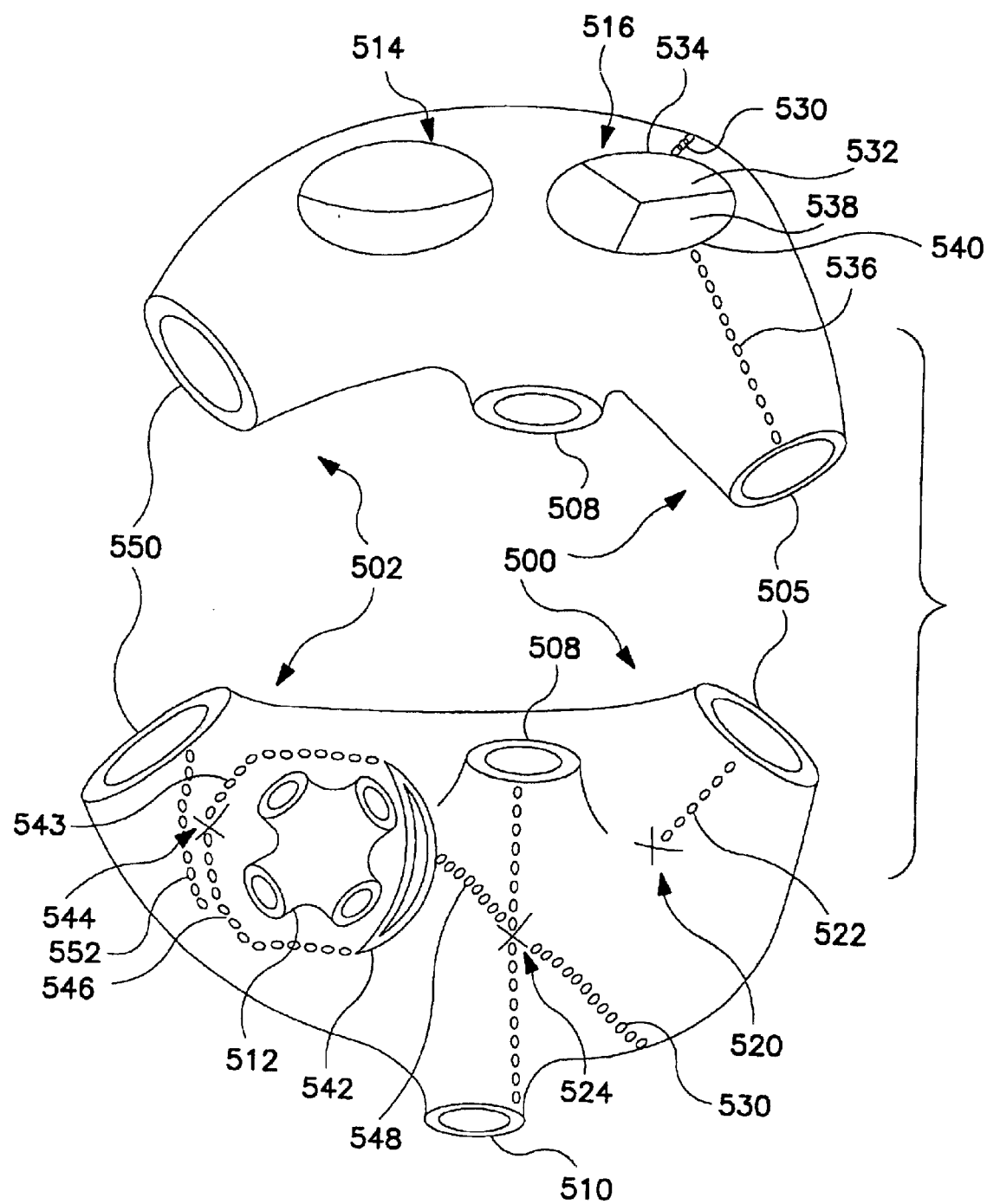

FIG. 6K illustrates the next step of the procedure, comprising the creation of lesion 552. Lesion 552 may be created using the curved hemostat illustrated at FIGS. 5A and 5B to create a curved lesion departing from lesion 546 and extending to the opening 550 in the right atrial appendage. As with lesions 543 and 546, the lesion may be produced by inserting one jaw of the hemostat through the incision 542, and compressing the left atrial wall between the jaws of the hemostat. Lesion 552 might also be performed prior to removal of the left atrial appendage, in conjunction with creation of lesions 543 and 546. In some embodiments of the invention, lesion 542 might be replaced by a simple incision extending from the opening 550 of the remnant of the left atrial appendage, and then later repaired by sutures.

Figure 6L:
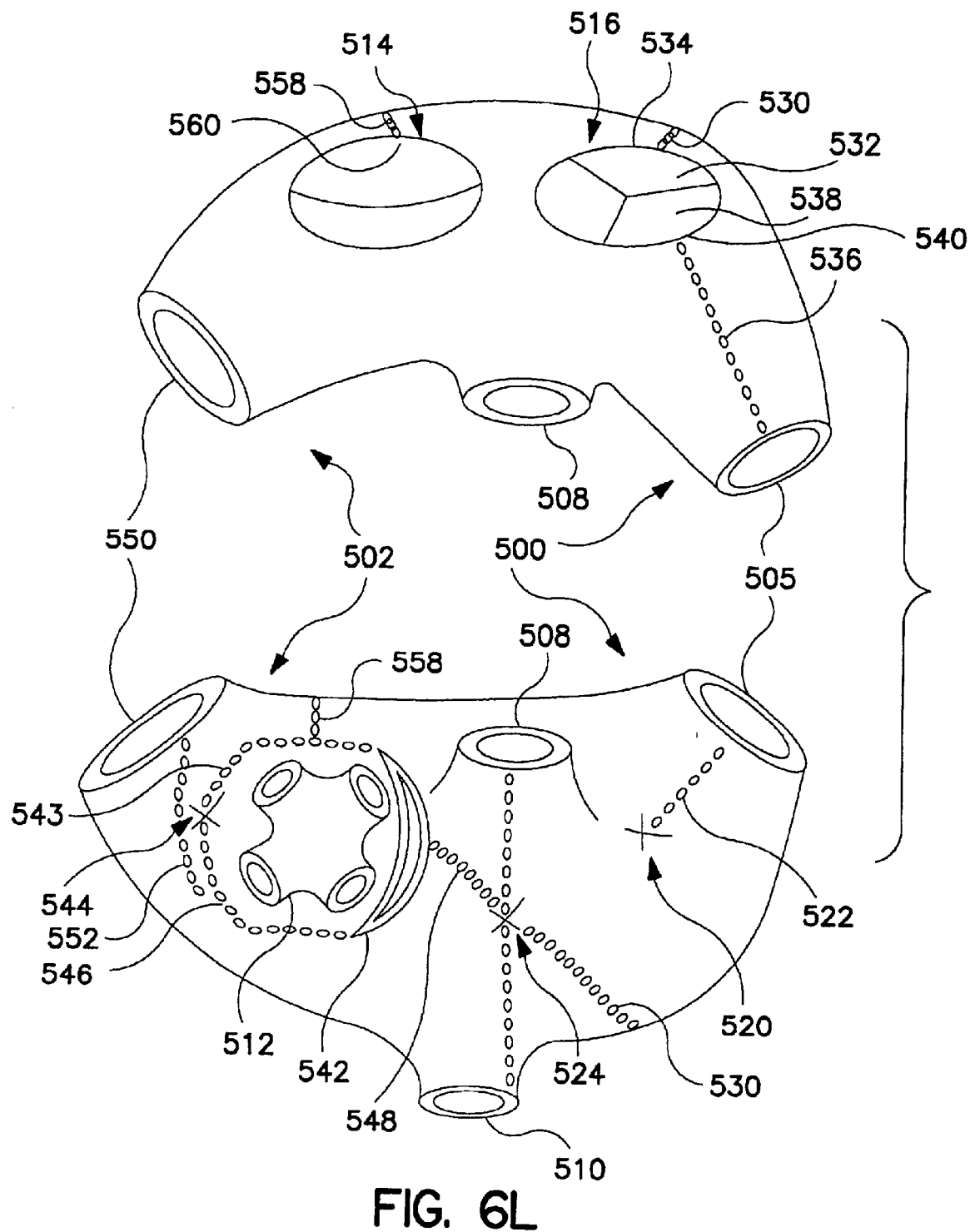

FIG. 6L illustrates the next step of the procedure, comprising the creation of lesion 558. Lesion 558 is created using the curved hemostat of FIGS. 5A and 5B, one jaw being inserted through incision 542 and compressing the left atrial wall between the jaws of the hemostat to create a lesion extending from lesion 543 to the mid point 560 of the annulus of the posterior mitral valve. Lesion 558 corresponds to the incision illustrated at step S as described in the Doty reference. Care must be exercised during this incision to prevent damage to the circumflex artery and the coronary sinus. Optionally cryo-ablation may be provided at the mid-point 560 of the posterior mitral valve annulus, by means of a cyro-probe introduced through the opening 550 through the remnant of a left atrial appendage, or through incision 542. In more limited access surgeries, cryo ablation may be provided by means of transvenous cyro-ablation catheter. Cryo-ablation corresponds generally to that illustrated at step J as described in the Doty reference.

Figure 6M:
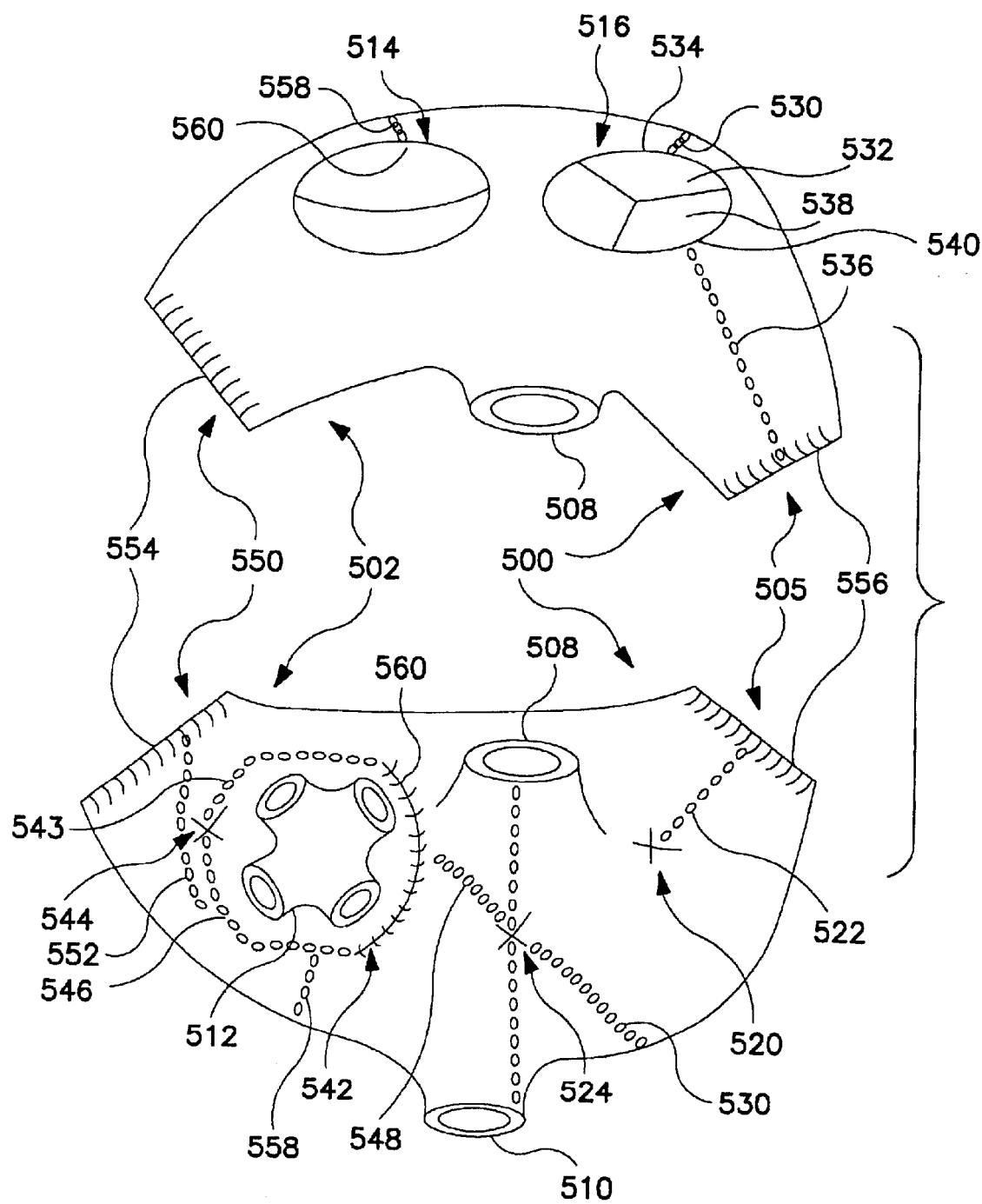

FIG. 6M illustrates the final steps of the procedure, comprising closing of the openings 505 and 550 into the remnants of the right and left atrial appendages, respectively, by means of sutures 554 and 556. As noted above, in the event that thoracoscopic surgical implements are employed, these openings may have previously been closed in conjunction with their creation, by means of staples, or otherwise, by means of thoracoscopic surgical tools. In addition, incision 542 is shown as closed by means of sutures 560 as discussed above, in some embodiments, incision 542 may have been replaced by simple puncture incision, which might be closed by means of staple, sutures, or otherwise, applied thoracoscopically. Access in incision 524 is similarly closed at this time.

The hemostats as illustrated in FIGS. 1A through 5B, discussed above, have the general configuration of conventional hemostats, as would be employed in the context of an open chest procedure. In the event that the procedure is adapted to a thoracoscopic procedure, similarly configured hemostat jaws may be employed on thoracoscopically introduced instruments to create the various lesion patterns. It is also envisioned that some modifications to the specific configurations of the disclosed hemostats may be desirable in conjunction with adapting the hemostats to thoracoscopic use or, in conjunction with adapting the hemostat set to other versions of the Maze or Maze type procedures. Such modifications are believed to be within the scope of the invention.

While all of the hemostats disclosed in the present application are preferably provided with R-F electrodes to create elongated lesions, it is believed the invention may also usefully be practiced in conjunction with hemostats employing microwave, heat, cyroablation, laser or other ablative techniques to create the various lesions provided by the method. Further, while the hemostats disclosed in the present application are provided with a single elongated electrode extending along each jaw, embodiments in which multiple electrodes arrayed along each jaw are employed are also believed useful in practicing the invention in some cases.

Therefore, the above disclosure should be considered as exemplary, rather than limiting, with regard to the following claims.

In conjunction with the above specification, we claim:

1. A method of treatment of a patient having atrial tachyarrhythmias, comprising:

selecting a set of hemostats having elongated opposing jaws each carrying means for applying ablation energy along the jaws, the set of hemostats including at least one hemostat having jaws with straight segments and at least two hemostats having jaws with curved segments of differing radii of curvature;

successively selecting individual hemostats within the set of hemostats and arranging the jaws of the selected individual hemostats along opposite sides of walls of the patient's atria and applying ablation energy to the walls of the patient's atria by means of the applying means to create lines of lesion corresponding generally to incisions employed in a Maze type surgical procedure.

2. A method as in claim 1, wherein arranging the jaws of the selected individual hemostats comprises inserting one jaw of a selected individual hemostat within a chamber of one of the patient's atria.

3. A method as in claim 2 wherein inserting one jaw of a selected individual hemostat comprises inserting the jaw through a wall of the chamber.

4. A method as in claim 3 wherein inserting one jaw of a selected individual hemostat comprises inserting the jaw through an incision through the wall of the chamber.

5. A method as in claim 3 or claim 4 wherein arranging the jaws comprises compressing the wall of the chamber between the jaws of the selected individual hemostat.

6. A method as in claim 5, comprising removal of the patient's atrial appendages.

7. A method as in any of claims 1–4, comprising removal of the patient's atrial appendages.

8. A method as in any of claims 1–4, wherein selecting individual hemostats comprises selecting bipolar electrosurgical hemostats having electrodes extending along the straight and curved segments of their jaws.

9. A method as in claim 8 wherein selecting individual hemostats comprises selecting hemostats having means for delivery of conductive fluid along the electrodes.

10. A method as in any of claims 1–4, further comprising employing cryoablation to complete at least one line of lesion.

11. A method as in any of claims 1–4, further comprising employing a surgical incision to complete at least one line of lesion.

* * * * *